United States Patent [19]
Tritsch

[11] 3,971,380
[45] July 27, 1976

[54] DISPOSABLE DIAPER HAVING AN ADHESIVE CLOSURE SYSTEM AND METHOD OF CONSTRUCTION THEREFOR

[75] Inventor: Ludwig Tritsch, Wilmette, Ill.
[73] Assignee: Johnson & Johnson, New Brunswick, N.J.
[22] Filed: May 19, 1975
[21] Appl. No.: 578,556

[52] U.S. Cl. ............................. 128/287; 128/284
[51] Int. Cl.² ....................................... A61F 13/16
[58] Field of Search ............ 178/284, 270, 290, 287

[56] References Cited
UNITED STATES PATENTS

| | | | |
|---|---|---|---|
| 3,575,175 | 4/1971 | McGuire | 128/290 R |
| 3,638,651 | 2/1972 | Torr | 128/284 |
| 3,840,013 | 10/1974 | Mesek | 128/284 X |
| 3,869,761 | 3/1975 | Schaar | 128/284 X |
| 3,901,237 | 8/1975 | Cepurtis | 128/284 |

Primary Examiner—Lawrence Charles

[57] ABSTRACT

A disposable diaper having a moisture-impermeable backing sheet and a moisture-retaining layer superposed on the backing sheet and including a facing sheet substantially coextensive with the backing sheet is provided with an adhesive closure system which comprises a composite made up of a plurality of superposed adhesive layers having different physical properties. An anchoring adhesive layer is adhesively attached to the backing sheet and to the facing sheet, and a securing adhesive layer is provided on the facing sheet, preferably adhesively attached to the anchoring layer through the facing sheet, and presents a tacky surface facing in the same direction as the exterior surface of the diaper facing sheet. Transfer tape is used to deposit individual layers of adhesive so as to form the composite.

3 Claims, 4 Drawing Figures

DISPOSABLE DIAPER HAVING AN ADHESIVE CLOSURE SYSTEM AND METHOD OF CONSTRUCTION THEREFOR

BACKGROUND OF THE INVENTION

This invention relates to disposable diapers. More particularly, this invention relates to disposable diapers adapted to be secured about an infant by means of adhesive closures.

Disposable diapers provide substantial convenience over conventional diapers and usually are secured about an infant by means of adhesive tape tabs which are affixed to the diaper along longitudinal edges thereof. The tabs extend laterally outwardly from opposite sides of the diaper. Typical of prior art adhesive systems is that illustrated by U.S. Pat. No. Re. 26,151 to Duncan et al. However, the outwardly extending tape tabs tend to interfere with manufacturing and packaging machinery during diaper fabrication. Another type of adhesive closure system is illustrated by U.S. Pat. No. 3,638,651 to Torr which shows diaper corner areas coated with a pressure-sensitive adhesive primarily intended for adhesive-on-adhesive contact for proper attachment. Complementary areas along the transverse edges of the diaper are coated with a release material to protect the exposed adhesive surfaces of an adjacent diaper packaged in the same container. However, the relatively large amounts of adhesive and release materials that would have to be used on each diaper would render the areas along the transverse edges of the diaper, i.e., that portion of the diaper which ultimately envelops an infant's waist, undesirably stiff. Moreover, the release material on the diaper inside surface contacts the infant's skin when the diaper is worn and could cause irritation thereof. Also, in some instances the body-contacting layer of the diaper is made of a fibrous, non-woven web which may not be strong enough to support an adhesive closure by itself. U.S. Pat. No. 3,840,013 to Mesek discloses a diaper having a tape closure system wherein longitudinally-extending adhesive areas are provided on the diaper facing layer.

SUMMARY OF THE INVENTION

The present invention contemplates a disposable diaper having pressure-sensitive adhesive areas situated within the perimetric limits of the diaper and which are made up of adhesive layers having different physical properties. The disposable diaper includes a flexible backing sheet of substantially moisture-impermeable material which forms a diaper outside surface, a moisture-retaining layer having a pad of absorbent material superposed on the backing sheet and attached thereto, a moisture-permeable porous facing sheet which is substantially coextensive with the backing sheet and forms a diaper inside surface, and a pressure sensitive adhesive closure made up of several adhesive layers. A layer of anchoring adhesive is provided between the backing sheet and the facing sheet at a marginal location on the diaper and is adhesively attached to the backing sheet and to the facing sheet. A layer of pressure sensitive securing adhesive, substantially coextensive with the anchoring adhesive, is provided on the facing sheet, presents a tacky surface in the same direction as the diaper inside surface, and can be adhesively attached to the anchoring adhesive through the porous facing sheet. The anchoring adhesive layer has a greater adhesion to the backing sheet than the securing adhesive layer; however, the latter has a greater quick stick to the backing sheet than the anchoring adhesive layer. The adhesive bonding of the facing sheet to the backing sheet at the diaper regions which are used for closure provides an integral structure of improved strength in the diaper areas which are subjected to stresses as the infant wearing the disposable diaper moves about.

The pressure sensitive adhesive closures for a disposable diaper can be readily constructed by using a transfer tape to position and deposit one or more of the several adhesive layers in a desired sequence. The method of this invention comprises the steps of depositing a layer of pressure sensitive anchoring adhesive onto a marginal area of the diaper backing sheet, superposing over the deposited anchoring adhesive a portion of the porous facing sheet so as to establish a region of adhesive contact therebetween, and depositing a layer of pressure sensitive securing adhesive onto the porous facing sheet and substantially coextensive with the region of adhesive contact between the backing sheet and the facing sheet so as to establish adhesive contact between the securing adhesive and the facing sheet. After the securing adhesive is deposited by means of a transfer tape segment onto the facing sheet, the transfer tape segment can be left in place to serve as a cover strip for the adhesive closure which protects the tacky surface thereof until the diaper is ready for use.

In instances where the porous facing sheet is of sufficient strength, the securing adhesive layer need not be adhesively bonded to the anchoring adhesive layer; however, for optimum closure strength it is preferable to urge both superimposed adhesive layers towards each other so as to establish adhesive-on-adhesive contact therebetween through the porous facing sheet the fibrous constituents of which also provide reinforcement for the produced adhesive laminate.

DESCRIPTION OF THE PREFERRED EMBODIMENTS

Figure 1:
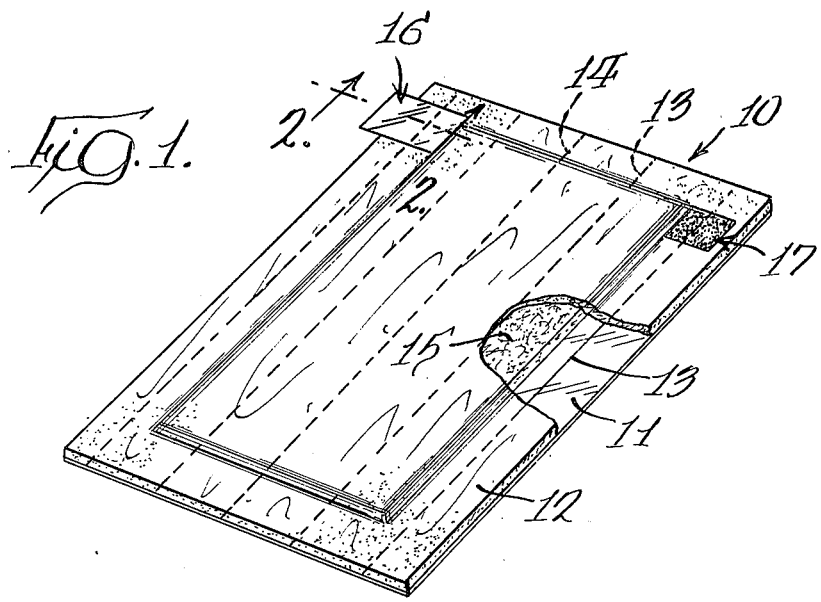
FIG. 1 is a perspective view of a disposable diaper embodying this invention.

Referring to FIG. 1, disposable diaper 10 includes moisture-impermeable backing sheet 11 which forms a diaper outside surface for direction away from an infant, moisture-permeable facing sheet 12 substantially coextensive with backing sheet 11 and attached thereto by means of adhesive beads such as beads 13 and 14, and absorbent pad 15 which is sandwiched between facing sheet 12 and backing sheet 11. Pad 15 is also anchored to backing sheet 11, e.g., by means of adhesive beads such as bead 14, and together with facing sheet 12 form the moisture-retaining layer of diaper 10. Sheet 12 usually is made of a porous, fibrous, non-woven material and provides a relatively soft facing which forms a diaper inside surface for direction toward the infant.

Adhesive closures 16 and 17 are provided at marginal locations of diaper 10 and near the longitudinal edges thereof. Closure 16 is shown in FIGS. 1 and 2 with protective cover strip 18 in place over a tacky surface of closure 16 whereas closure 17 is shown with the cover strip removed and the tacky surface thereof exposed and ready for securement.

Figure 2:
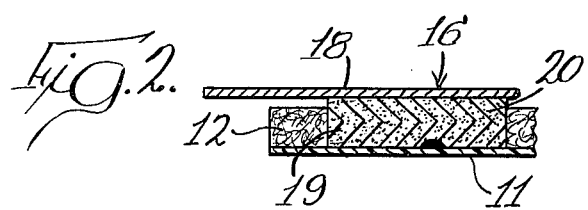
FIG. 2 is a sectional elevation, on an enlarged scale, taken along plane 2—2 in FIG. 1.

Referring to FIG. 2, adhesive closure 16 comprises pressure sensitive anchoring adhesive layer 19 forming an adhesive bond with the inside surface of backing sheet 11 and with an overlying portion of facing sheet 12. Securing adhesive layer 20, also of the pressure sensitive type, is adhesively attached to facing sheet 12 and superposed over anchoring adhesive layer 19 substantially coextensively therewith. A portion of securing adhesive layer 20 is submerged within facing sheet 12 and adhesive-on-adhesive contact is established between adhesive layers 19 and 20 through porous facing sheet 12. In this manner an integral closure structure is produced within the peripheral limits of diaper 10, attached to backing sheet 11 and presenting a tacky surface facing in the same direction as the inside surface of the diaper. By selecting appropriate pressure sensitive adhesive formulations for each of the aforementioned adhesive layers, as will be discussed in greater detail hereinbelow, the closure can be designed to provide optimum quick tack for ready securement of the diaper about an infant while at the same time providing a strong, fiber-reinforced adhesive bond between the closure and the closure-supporting portion of the diaper. Cover strip 18 protects the tacky surface of adhesive layer 20.

Figure 3:
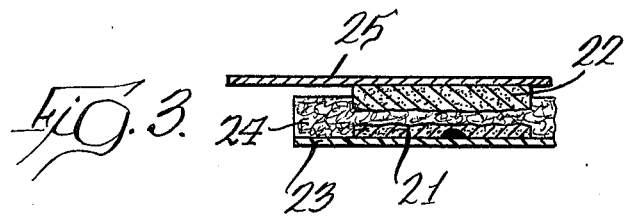
FIG. 3 is a sectional elevation similar to that of FIG. 2 and showing yet another embodiment of the present invention.
Figure 4:
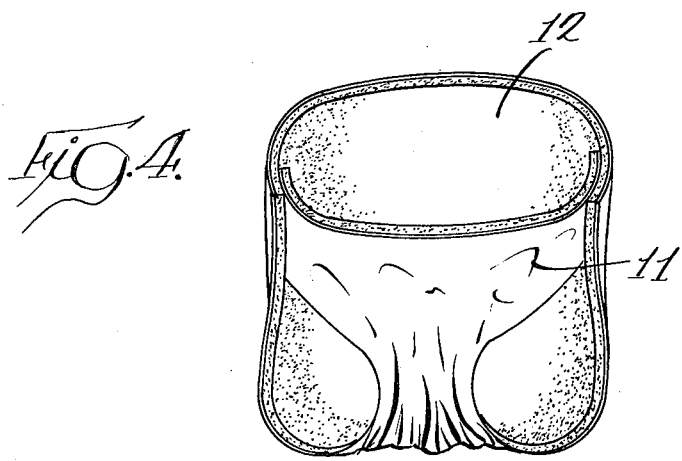
FIG. 4 is a perspective view illustrating the configuration assumed by the disposable diaper of this invention when applied about an infant.

Another embodiment is illustrated in FIG. 3, wherein there exists no initial adhesive-on-adhesive contact between anchoring adhesive layer 21 bonded to diaper backing sheet 23 and securing adhesive layer 22 bonded to diaper facing sheet 24. Cover strip 25 protects the tacky surface of securing layer 22. In instances where the strength of the facing sheet is sufficient for an effective retention of the diaper about an infant, the embodiment shown in FIG. 3 may be utilized and the aforementioned adhesive-on-adhesive contact may not be essential, albeit desirable. However, in many instances adhesive-on-adhesive contact will be established in the embodiment of FIG. 3 by the mother or nurse attending the infant as a slight finger pressure is applied to the diaper closure urging the tacky surface of the closure against a juxtaposed region of the diaper backing sheet after the diaper has been applied about an infant and has assumed the configuration shown in FIG. 4.

The securing adhesive layer is formulated to provide optimum quick stick properties to the diaper backing sheet once the cover strip protecting the tacky surface thereof is removed. This adhesive layer must also have adequate shear resistance to perform satisfactorily in the intended diaper application. Adhesive formulations based on natural and synthetic rubbers tackified with wood rosin derivatives or polyterpene resins can be used for this purpose. Adhesives produced from styrene-isoprene and styrene-butadiene block copolymers tackified with hydrocarbon resins and extended with mineral oil can also be employed. Adhesives can also be produced from polyacrylates, such as polymers of 2-ethylhexyl acrylate or copolymers thereof with vinyl acetate, maleic or fumaric dialkyl esters, acrylonitriles, or other monomers that have a stiffening effect on the polymer composition. Pressure sensitive adhesives of other types also are known and have been found useful.

Typical securing adhesive layers suitable for use in the present invention have Probe Tack Values of at least 100 grams, as determined on a Polyken Probe Tack Tester Model 80-2, manufactured by Testing Machines, Incorporated, Amityville, New York. Values are obtained with a rough surfaced polyethylene probe, using a pressure of 100 g./cm.$^2$, dwell time of 0.2 seconds, and a probe separation speed of 2 seconds. Preferred 180 degree Peel Adhesion as determined by the standard test of the Pressure Sensitive Tape Council (PSTC-1) but using a ¼ inch thick extruded high density polyethylene test plate is at least 36 oz./inch. For example, an adhesive which will meet the foregoing requirements can be prepared from the following components:

Formulation A:

| | |
|---|---|
| Styrene-Isoprene Block Copolymer | 90–100 parts by wt. |
| Styrene-Butadiene Block Copolymer | 10–0 parts by wt. |
| Synthetic Polyolefin Tackifying Resin (Soft. Point 85–95°C.) | 100–150 parts by wt. |
| Mineral Oil | 20–40 parts by wt. |
| Antioxidant | 2 parts by wt. |

The anchoring adhesive layer provides good adhesion to the diaper backing sheet. Inasmuch as the adhesive layer deposited during manufacture of the diaper has plenty of time to develop full adhesion while the diaper moves through the normal channels of trade before the ultimate use thereof, the quick stick properties of the anchoring adhesive layer are relatively unimportant. Also, during manufacturing higher pressures can be applied to the diaper as the adhesive layer is urged thereagainst than would be applied while the diaper is placed about an infant. However, in order to avoid situations where the facing sheet may become parted from the backing sheet after the diaper is secured about an infant, it is necessary that the anchoring adhesive layer has a greater adhesion to the backing sheet than the securing adhesive layer. To this end a peel adhesion of at least about 64 oz./in. as determined by the standard test of the Pressure Sensitive Tape Council PSTC-1) is preferred. Anchoring adhesive layers can be made from adhesive formulations based on styrene-butadiene block copolymers and blends thereof, styrene-isoprene block copolymers tackified with hydrocarbon resins, wood rosin derivatives, or terpene phenolic resins, as well as on natural or synthetic rubbers tackified with a variety of relatively high softening point thermoplastic tackifying resins commonly used in pressure sensitive adhesives. Adhesives containing heat reactive systems may also be employed to increase cohesive strength of the adhesive, but flexibility of the adhesive must be retained. Adhesives produced from polymers of alkyl acrylates, or copolymers thereof, may also be used, but will generally not give as high an adhesion to polyethylene as can be obtained with other above mentioned adhesives. Typical compositions useful as an anchoring adhesive can be prepared from the following components:

Formulation B:

| | |
|---|---|
| Styrene-Butadiene Block Copolymer | 80–100 parts by wt. |
| Polymerized alpha-Pinene Tackifying Resin (Soft. Point 115°C.–135°C.) | 100 parts by wt. |
| Mineral Oil | 0–5 parts by wt. |

-continued

| | |
|---|---|
| Antioxidant | 2 parts by wt. |

Formulation C:

| | |
|---|---|
| Styrene-Butadiene (Random Copolymer) | 75 parts by wt. |
| Natural Rubber | 25 parts by wt. |
| Polymerized beta-Pinene Tackifying Resin (Soft. Point 115°C.–125°C.) | 20 parts by wt. |
| Pentaerythritol Ester of Hydrogenated Wood Rosin | 20 parts by wt. |

The several adhesive layers can be readily deposited onto the disposable diaper structure utilizing segments of transfer tape bearing an adhesive layer having the desired properties. A preferred method of manufacture according to the present invention is illustrated by the following sequence of manipulative steps which can be used to produce disposable diapers equipped with the present closure system.

The terminal portion of a release-coated ribbon, e.g., a silicone-coated release paper, is provided on one side with a securing adhesive layer of Formulation A and on the other side with an anchoring adhesive layer of Formulation B. Both adhesive layers are substantially coextensive with each other, albeit situated on opposite sides of the release-coated ribbon. The terminal portion bearing the adhesive layers is then inserted between juxtaposed webs of diaper backing sheet and diaper facing sheet so that the anchoring adhesive layer faces the inside surface of the backing sheet. Thereafter the anchoring adhesive layer is brought into contact with the inside surface of the backing sheet and adhered thereto at a marginal area thereof.

Subsequently, the release-coated ribbon is pulled back releasing the anchoring adhesive layer which remains adhered to the backing sheet, turned about 180° about the longitudinal axis of the release-coated ribbon, and positioned so that the securing adhesive layer faces the diaper inside surface defined by the facing sheet above the earlier-deposited anchoring adhesive layer. Alternatively, the securing adhesive layer can also be supplied by means of a separate transfer tape segment or ribbon. In any event, the securing adhesive layer is then brought into contact with the diaper inside surface and is partially extruded through the facing sheet by applying appropriate pressure so that the securing adhesive layer is adhered also to the underlying anchoring adhesive layer and the latter is securely bonded to the backing sheet. The release-coated ribbon is left in place and serves as a protective cover strip for the securing adhesive layer. If desired, the release-coated ribbon can have differential release properties on each side thereof so that during assembly of the diaper the anchoring adhesive layer is more readily released therefrom than the securing adhesive layer.

As pointed out hereinabove, cover strips 18 and 25 can be derived from the transfer tape ribbons or segments and can be smooth plastic film having a relatively non-adhering surface, paper coated with a silicone release compound, or similar release sheet materials.

Several different types of facing materials may be used for diaper facing sheets 12 and 24. For example, facing sheets 12 and 24 may be made up of a mixture of fibers comprising predominantly inexpensive short cellulosic fibers such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheets 12 and 24 may also be made of an apertured, nonwoven fabric which is formed, for example, in accordance with the teachings of commonly assigned U.S. Pat. Nos. 2,862,251; 3,081,514; and 3,081,515. Briefly, such fabrics are moisture-permeable, porous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd.$^2$.

In addition, the facing sheets can be formed of a nonapertured material, such as nonwoven isotropic web, or the like. In all of the aforementioned facing materials, the material should be relatively hydrophobic so as to retard wicking within the facing layer.

Highly moisture-absorbent fibrous pad or batt 15, which usually is substantially rectangular in shape but smaller than the facing sheet and the backing sheet, is centrally disposed between facing sheet 14 and backing sheet 11. Pad 15 is usually anchored to backing sheet 11 by means of an adhesive bead, heat sealing, or similar expedients. Pad 15 can be formed in accordance with the teachings of U.S. Pat. No. 3,612,055 to Mesek et al. If desired, a highly moisture-absorbent layer can be provided substantially coextensive with backing sheet 11 and facing sheet 12.

A suitable backing sheet material for the diapers embodying the present invention can be a polyalkylene web such as an opaque polyethylene web about 0.001 inch thick. Another suitable material for this purpose is a polyethylene terephthalate web having a thickness of about 0.0005 inch. Typical disposable diapers which can be provided with the adhesive closures described hereinabove are shown in U.S. Pat. No. 3,612,055 to Mesek et al. and in U.S. Pat. No. 3,683,916 to Mesek et al. Other suitable disposable diaper structures which can be improved by the present adhesive closures are shown in U.S. Pat. No. Re. 26,151 to Duncan et al.

In use, a diaper equipped with the adhesive closures of the present invention is applied to the infant by laying out the diaper on a suitable flat surface and placing the infant thereon so that the waist-underlying end of the diaper is that having the fastener means. The other end of the diaper then extends downwardly between the infant's legs. Next, the downwardly-extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive closures are prepared for use by removing the cover strips from the tacky surfaces thereof. The diaper is then secured in the desired position about the infant by simply urging the exposed tacky surfaces in contact with the adjacent outer surface of the diaper. The applied diaper assumes the configuration illustrated in FIG. 4.

The foregoing description and the drawing are illustrative but are not to be taken as limiting. Still other variations and modifications are possible without departing from the spirit and scope of the present invention.

I claim:

1. A disposable diaper having an inside surface for direction toward an infant when the diaper is worn by that infant and an outside surface for direction away from said infant and including a flexible backing sheet of substantially moisture-impermeable material forming the diaper outside surface, a moisture-retaining layer having a pad of absorbent material superposed on said backing sheet and attached thereto and a porous facing sheet substantially coextensive with said backing sheet and forming the diaper inside surface, and a pressure sensitive adhesive closure within the peripheral limits of the diaper and comprising a layer of anchoring adhesive between said backing sheet and said facing sheet at a marginal location on said diaper and adhesively attached both to said backing sheet and to said facing sheet and a layer of pressure sensitive securing adhesive on said facing sheet, substantially coextensive with said layer of anchoring adhesive and adhesively attached to said anchoring adhesive through said facing sheet and presenting a tacky surface in the same direction as the diaper inside surface; said anchoring adhesive layer having greater adhesion to the backing sheet than said securing adhesive layer, and said securing adhesive layer having a greater quick stick property relative to the backing sheet than said anchoring adhesive layer.

2. The disposable diaper in accordance with claim 1 wherein said securing adhesive layer comprises a styrene-isoprene block copolymer tackified with a polyolefin.

3. The disposable diaper in accordance with claim 1 wherein said anchoring adhesive layer comprises a styrene-butadiene copolymer tackified with a pinene resin.

* * * * *